United States Patent [19]

Manalastas et al.

[11] Patent Number: 5,188,654

[45] Date of Patent: Feb. 23, 1993

[54] COATINGS WITH IONICALLY AND COVALENTLY CROSSLINKED NEUTRALIZED CARBOXYLATED POLYMERS

[75] Inventors: Pacifico V. Manalastas, Edison; Evelyn N. Drake, Bernardsville; Warren A. Thaler, Flemington; Edward N. Kresge, Watchung; Chester W. Elspass, Alpha, all of N.J.; Albert J. Geiger, Fort Saskatchewan, Canada; Vijay Swarup, Clinton, N.J.

[73] Assignee: Exxon Research and Engineering Company, Florham Park, N.J.

[21] Appl. No.: 676,606

[22] Filed: Mar. 28, 1991

[51] Int. Cl.⁵ ............................. C05C 9/00; C05G 3/10
[52] U.S. Cl. ...................................... 71/28; 71/64.07; 71/64.11; 71/64.13; 428/334

[58] Field of Search ................. 71/28, 64.07, 64.11, 71/64.13; 428/334

[56] References Cited

U.S. PATENT DOCUMENTS 4,741,956  5/1988  Thaler et al. .................. 428/334

Primary Examiner—Ferris Lander
Attorney, Agent, or Firm—Jay Simon

[57] ABSTRACT

A composite comprising a substrate and a polymeric coating adhered to at least one surface of said substrate, said polymer coating having a thickness of about 1 to about 100 micrometers, wherein said polymer coating comprises an ionically and covalently crosslinked neutralized carboxylated polymer having a carboxylate content of about 5 to about 300 meq. per 100 grams of said ionically and covalently crosslinked neutralized carboxylated polymer.

8 Claims, No Drawings

COATINGS WITH IONICALLY AND COVALENTLY CROSSLINKED NEUTRALIZED CARBOXYLATED POLYMERS

FIELD OF THE INVENTION

The present invention relates to polymeric coatings having improved barrier properties wherein the polymeric coating is a covalently crosslinked neutralized carboxylated polymer.

The present invention relates to controlled release fertilizers and particularly to fertilizer-pesticide compositions. The invention is more particularly directed to fertilizers and fertilizer-pesticide compositions to which thin film or ultrathin films or coatings of covalently crosslinked neutralized carboxylated polymers have been applied as an improved controlled release agent. Related to this, the present invention is directed to methods for producing fertilizer and fertilizer-pesticide composites coated with covalently crosslinked neutralized carboxylated polymers in addition to agricultural processes involving the use of such coated fertilizers and fertilizer-pesticide composites. In this regard, agricultural processes in which the fertilizer and fertilizer-pesticide composites coated with covalently crosslinked neutralized carboxylated polymers in accordance with the present invention may be applied include processes for enhancing vegetation including plant growth stimulation and regulation as well as stimulation of seed germination.

DESCRIPTION OF PRIOR ART

Solids (e.g., substrates, pipes, slabs, sheets, etc.) can be protected from the external environment with the use of barrier or protective coating materials. For protection from water or moisture, polymer or organic materials are widely used. For cost effectiveness, however, these materials are generally applied as thin films. The thickness of the film depends upon the desired degree of water protection. The thicker the film the more likely that water penetration would be slowed down. In practice, applying an effective thin coating is difficult because of the various stresses tending to make the film discontinuous (e.g., film-rupture, pin holes). Films will rupture when a threshold stress is exceeded. The lateral stress tending to rupture a film is inversely proportional to an exponential power of the film thickness. The thinner the film, the more easily it will rupture.

There are many applications for thickened or gelled solutions of polymers in organic liquids which are quite diverse. There are also a number of physical and chemical techniques for preparing such systems. The present invention concerns a process for forming a polymer coating having improved barrier properties.

Coatings which can be protective, decorative or special purpose are usually applied at thicknesses of as high as 150 micrometers or thicker in order to provide the desired properties required of such coatings. Such high thicknesses are required in order to compensate for coating defects or for poor coating material properties.

Coatings with improved properties may be applied as thin films having a thickness range of 1–100 micrometers, with a preferred range of 2–40 micrometers. In order for such coatings to be functional, the coating material should show improved barrier properties and be a continuous film with few or no defects.

The discovery of the film forming properties of ionically and covalently crosslinked carboxylated polymers has made possible the extension of their use to coating applications, including controlled release products in agriculture (e.g., controlled release fertilizer). In controlled release fertilizer applications coatings of ionically and covalently crosslinked carboxylated polymers will act as barriers to water soluble constituents of the fertilizer, shielding them from premature release in aqueous environments for periods ranging from several days to several months. Because of their unique barrier properties ionically and covalently crosslinked carboxylated polymers can potentially be used to make cost effective controlled release fertilizers. The benefits obtained by the use of these coatings can include labor savings, increased crop yield, increased nitrogen utilization efficiency and time savings. The amount of premium is proportional to the cost of coating used on the controlled release product. Therefore, it is of economic importance to use as little coating material as possible to make a desirable agricultural product. The amount of coating which should be applied on the controlled release product, however, is not only dictated by economic considerations, but also by the required performance. In most cases the performance requirements include the control of the release or dissolving property of the agricultural material, achievable with the application of coatings free of fine pinholes or defects. Herein lies the major problem in controlled release fertilizer, particularly with existing conventional coatings, because the thinner the coating or the less coating material is applied the less likely that defect free coatings can be made. Thus, commercially available controlled release fertilizer products are with thick (>40 microns) coatings to yield acceptable performance (e.g., <20% release of water soluble nutrient in seven days in water at 20° C.). As a consequence, these products are expensive and have found limited uses. With the discovery of ionically and covalently crosslinked carboxylated polymers coatings, however, the application of thin (<40 microns), defect-free films on controlled release fertilizer can now be achieved, thus, its use presents a potential route for making affordable controlled release fertilizer.

The instant invention teaches that a solution of a neutralized carboxylated polymer with a covalent crosslinking means can meet many of the requirements for forming an improved thin film coating.

Carbon, hydrogen, oxygen, nitrogen, phosphorus and sulphur are the primary elements essential to plant growth. Soils contain all of these elements in addition to other macro and micronutrients that enhance plant growth. Typically, however, such elements are seldom present in the soil in sufficient quantity or in forms that can support maximum plant productivity and yield. Therefore, fertilizers having specific chemical formulations and in pre-determined amounts must be added to enrich the soil to ensure maximum plant yield. The amount and form of the fertilizer added are pre-determined by chemically assaying the amount and availability of the required nutrient(s) in the soil, for example, as disclosed by Methods of Soil Analysis, 1982, Amer. Soc. Agronomy, Madison, Wis. Thus, appropriate fertilizer is added in amounts calculated to ensure the required plant yield based on known fertilizer response curves established by extensive agronomic testing for the particular plant and plant growth environment.

Fertilizers containing nitrogen, phosphorus, sulphur and/or potassium, by way of example, may be applied as solid granules or in liquid form. These primary fertilizers may be supplemented with certain trace elements such as copper, iron, manganese, zinc, cobalt, molybdenum, boron usually supplied as oxides or salts containing the elements in the cationic form. Suitable salts are, for example, sulphates, nitrates, chlorides, molybdates or borates. The difference between trace element deficiency and toxicity, however, is but a few parts per million as measured by the concentration of the element in the soil. Moreover, the efficiency of utilization of fertilizers, i.e., the percent uptake of the applied fertilizers is notoriously low. In this regard, chemical, biological and physical processes compete with the plant for the added fertilizer nutrients usually to the detriment of plant productivity. In addition, nitrogen fertilizers added to the soil may be leached into groundwater, chemically immobilized into clay minerals, chemically removed by volatilization of ammonia, biologically removed from the soil by denitrification to dinitrogen and nitrous oxide gases or immobilized into the active microbial biomass. These competing and simultaneous occurrences result in fertilizer use efficiency of nitrogen often being less than 50%. Thus, when 100 kg N/ha is added to the soil, the plant actually "sees" only 50 kg N/ha. Although most soils contain high levels of phosphorus, it is chemically immobilized as calcium phosphates, e.g. in soils of pH >7.0 or iron and aluminum phosphates, e.g. in soils of pH <5.0, and is thus not plant-available. Fertilizer phosphorus applied to these soils, however, is rapidly immobilized resulting in fertilizer use efficiencies seldom exceeding 30%.

If the release of nutrients from fertilizers could be controlled to more closely match the actual physiological requirements of the plant for the nutrient and if temporary or permanent losses of the fertilizer nutrients could be minimized if not eliminated, several advantages would accrue:

i) less fertilizer would be required to achieve the same plant yield;

ii) the same amount of fertilizer could be applied resulting in higher yields and concomitant lower per unit plant production costs;

iii) less water-soluble nitrogen would leach into groundwaters thus minimizing ground-water pollution; and/or iv) less nitrogenous gases would evolve into the atmosphere thus minimizing damage to the fragile ozone layer.

Although it is known to protect solid substrates, such as pipes, slabs, sheets and the like from the external environment with the use of barrier or protective coating materials, this technology has not been applied in accordance with the present invention, particularly with respect to agricultural products. In conventional applications, however, polymers or other organic materials are widely used as coatings to provide protection from water or moisture. For cost effectiveness these materials are typically applied as thin films. The thickness of the film depends upon the desired degree of water protection. The thicker the film, the more likely that water penetration would be slowed down. In practice, applying an effective thin coating is difficult because of the various stresses tending to make the film discontinuous (e.g., film-rupture, pin holes). Films will rupture when a threshold stress is exceeded. The laterial stress tending to rupture a film is inversely proportional to an exponential power of the film thickness. The thinner the film, the more easily it will rupture. Polymers containing associating ionic groups, i.e. ionomers, which have a high degree of molecular interactions make excellent protective films. Covalently crosslinked networks of ionomers containing associating ionic groups can further improve the strength and barrier performance of the coatings.

There are many applications for thickened or gelled solutions of polymers in organic liquids. There are also a number of physical and chemical techniques for preparing such systems. The present invention, however, is concerned with polymeric coatings having improved properties which have been found to be particularly suitable for application to agricultural products, such as fertilizers, pesticides, herbicides, insecticides, bacteriocides, fungicides, nematicide, sporicides, and the like, in addition to combinations thereof.

DETAILED OF THE INVENTION

The present invention relates to a process for forming a polymeric coating having improved barrier properties from an organic solution of an organic liquid, a neutralized carboxylated polymer, and a means of covalent crosslinking.

In general, the present invention, therefore, relates to coating vegetation enhancement agents, such as fertilizers and fertilizer-pesticide combinations, with thin or ultra-thin coatings of ionically and covalently crosslinked carboxylate polymers to result in controlled release fertilizers and fertilizer-pesticide combinations having improved barrier properties, as well as agricultural processes involving methods of using fertilizers and fertilizer-pesticide combinations coated with ionically and covalently, crosslinked, carboxylate polymers in accordance with the present invention so as to decrease dissolution of soluble fertilizer components, increase fertilizer use efficiency and substantially decrease losses of the added fertilizer from the plant growth medium due to biological, chemical, or physical processes competing with the plant for the said nutrients.

DETAILED DESCRIPTION

The component materials of the instant invention generally include a water insoluble carboxylated polymer dissolved in an organic solvent system to form a solution with a concentration level of 0.1 to 20 weight percent, wherein the solution can contain a covalent crosslinking agent which is activated at a minimal temperature of 40° C. or alternatively, the polymeric coating can be crosslinked by a post coating crosslinking means. The solvent system comprises an organic solvent with or without a polar cosolvent, such as alcohols amines or ammonia. The solvent can be an organic liquid which is capable of dissolving the polymeric backbone. A cosolvent may be needed to break up associated domains resulting from aggregation of ionic species.

The present invention relates to a process for forming thin polymeric coatings which are both ionically and covalently crosslinked having improved barrier properties and physical properties from an organic solution of an organic liquid, a neutralized carboxylated polymer and a covalent crosslinking means.

The thin polymeric coatings are coated on vegetation enhancements, e.g., fertilizer or fertilizer/pesticide combinations. The process of the instant invention generally comprises an organic solution of a water insoluble carboxylated polymer with a crosslinking agent which is not activated until a temperature of 40° C. is obtained; coating the organic solution of the water insoluble carboxylated polymer and the crosslinking agent onto a substrate and subjecting the coated substrate to a temperature of at least 40° C. to activate the crosslinking agent thereby covalently crosslinking the carboxylated polymer. An alternative process comprises coating an organic solution of the water insoluble carboxylated polymer on the substrate and subsequently subjecting the coated substrate to an election beam thereby covalently crosslinking the water insoluble carboxylated polymer. A still alternate process comprises coating a substrate with an organic solution of the water insoluble carboxylated polymer and subsequently contacting the coated substrate with a vapor or solution of sulfur monochloride thereby forming a covalently crosslinked water insoluble carboxylated polymer. The sulfur monochloride can also be added to the organic solution of carboxylated polymer immediately prior to spray coating. It is contemplated within the scope of this invention that any two or more of these processes in conjunction could be used to crosslink the water insoluble carboxylated polymer. It is also contemplated that the water insoluble carboxylated polymer could be covalently crosslinked either in solution or in a solid form to form a formed polymeric article of 0.5 to 40 mils thickness by any one of the aforementioned processes.

The covalently crosslinked water insoluble carboxylated polymers of the instant invention will comprise from about 1 to about 500 milliequivalents of pendant carboxylate groups per 100 grams of polymer, more preferably from 5 to 300 meq. pendant carboxylated groups. The carboxylate groups are neutralized with counterions selected from, but not limited to, Groups IA, IB, IIA, and IIB of the Periodic Table of Elements, as well as lead, tin, zinc and antimony, or ammonium and amine counterions.

The degree of neutralization of the carboxylate groups of the covalently crosslinked neutralized carboxylated polymers may vary from 0 (free acid form) to 100 mole percent, preferably 50 to 100 mole percent. With the utilization of covalently crosslinked neutralized carboxylated polymers in this instant invention, it is preferred that the degree of neutralization be substantially complete, that is, with no substantial free acid present and without substantial excess of the base, other than that needed to ensure neutralization. The covalently crosslinked neutralized carboxylates possess greater thermal stability and better mechanical properties (such as toughness) compared to their acid form. Thus, it is clear that the polymers which are normally utilized in the instant invention comprise substantially neutralized carboxylated groups and, in fact, an excess of the neutralizing material may be utilized without defeating the objects of the instant invention.

The covalently crosslinked neutralized carboxylate polymers of the instant invention may vary in number average molecular weight from 1,000 to 10,000,000 preferably 5,000 to 1,000,000 most preferably from 10,000 to 600,000. These polymers may be prepared by methods known in the art, such as a copolymerization where one of the monomers is a carboxylate containing monomer.

Covalently crosslinked neutralized carboxylated polymers used in the instant invention are characterized by the formula:

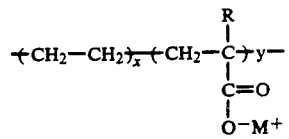

wherein y is about 0.1 to about 30 mole percent, more preferably about 0.5 to about 20, and most preferably about 1 to about 15; R is hydrogen, an ethyl or a methyl group; wherein M+ is selected from the group consisting of ammonium, amine counterions and metal counterions selected from, but not limited to, the group consisting of lead, antimony, zinc, tin and Groups IA, IB, IIA and IIB of the Periodic Table of Elements.

The concentration of the covalently crosslinked neutralized carboxylated polymer in the solution of the covalently crosslinked neutralized carboxylated polymer, covalent crosslinking agent and the organic solvent, and optionally the cosolvent, is about 0.1 to about 20 weight percent, more preferably about 0.5 to about 10, and most preferably about 0.5 to about 6.0.

The organic solvent is selected from the group consisting of aromatic solvents, oxygen-containing solvents, such as esters, ketones, ethers, aldehydes and carboxylic acids, and amines, amides, alcohols and mixtures thereof. Preferred organic solvents are tetrahydrofuran, acetic acid, xylene and toluene.

In order to reduce the viscosity of an organic solution of the neutralized carboxylated polymer so as to be able to employ the organic solution in a casting process, a polar cosolvent may be added to the organic solution of the neutralized carboxylated polymer to solubilize the pendant carboxylate groups. The polar cosolvent will have a solubility parameter of at least 10.0, more preferably at least 11.0, and may comprise from 0.01 to 15.0 weight percent, preferably 0.1 to 5.0 weight percent, of the total mixture of organic liquid, water insoluble neutralized carboxylated polymer and polar cosolvent.

Normally, the polar cosolvent will be a liquid at room temperature, however, this is not a requirement. It is preferred, but not required, that the polar cosolvent be soluble or miscible with the organic liquid at the levels employed in this invention. The polar cosolvent is selected from the group consisting essentially of alcohols, amines, ammonia, amides, acetamides, phosphates, or lactones and mixtures thereof. Especially preferred polar cosolvents are aliphatic alcohols, such as methanol, ethanol, n-propanol, isopropanol, 1,2-propane diol, monoethyl ether of ethylene glycol, n-ethylformamide and methyl isobutyl carbinol.

The polymeric coatings of the instant invention are formed by applying the organic solution of the carboxylated polymer and, optionally, the covalent crosslinking agent over the substrate at an ambient temperature of 10°-70° C., but at a temperature lower than the activation temperature of the covalent crosslinking agent, by either dipcoating or spray-coating or with the use of other techniques for thin spreading (such as brushing). The organic solvent system is then permitted to evaporate with or without the aid of forced drying gas, such as air or nitrogen gas. This step is called the drying process. The drying gas temperature can be from ambient temperature up to the boiling point of the organic solvent system. Preferably the temperature of the drying gas is between 20° C. to 100° C. The most preferred temperature of the drying gas should be about 50° C. to about 70° C. for fast evaporation of the organic solvent system. After drying the thickness of the applied coating should be about 1 micrometer to about 100 micrometers. Most preferred, the coating thickness should be about 2 to about 40 micrometers for both performance and economic reasons. To control the thickness of the applied coating, the solution concentration of the carboxylated polymeric and is applied at 0.5 to 10 weight percent. Most preferably, the concentration should be about 1 to 6 weight percent. The coating solution of the carboxylated polymer can be applied in single or multiple layers, depending on the desired coating thickness. In any instance, the organic solvent system is evaporated after each layer application. The carboxylated polymer can be applied over the substrate of interest or over a previous coating. In the latter case, such practice can modify or improve the performance of the coated system.

Covalent crosslinking of the above mentioned polymers can be carried out with a variety of common vulcanization formulations involving crosslinking peroxides, carriers for crosslinking peroxides, accelerators and sensitizers.

Examples of peroxide crosslinking agents include acetyl cyclohexane sulphonyl peroxide, bis (2-ethylhexyl) peroxydicarbonate, bis(4-tert butyl cyclohexyl) peroxydicarbonate, di-cyclohexyl peroxydicarbonate, di-n-propyl peroxydicarbonate, di-n-butyl peroxydicarbonate, dicetyl peroxydicarbonate, disecbutyl peroxydicarbonate, di-isopropyl peroxydicarbonate, tert butyl peroxyeodecanoate, bis (2,4-dichlorobenzoyl) peroxide, tert butyl peroxy pivalate, bis (ortho-methyl benzene) peroxide, bis (ortho-methyl benzoyl) peroxide, bis (3,5,5-trimethyl hexanoyl) peroxide, dilauaryl peroxide, di-decanoyl peroxide, di-octanoyl peroxide, di-proprionyl peroxide, di-benzoyl peroxide, tert butyl peroxy-2-ethylhexanoate, tert butyl peroxydiethylacetate, tert butyl peroxy isobutylate, bis (tert butyl peroxy isopropyl) benzene and others like them.

Possible carriers for the peroxide are contemplated to the calcium carbonate, clay, EVA copolymer masterbatch, EPDM-masterbatch, silicone oil, plasticizer as well as organic solvents.

Accelerators are contemplated to include thiazoles, sulfinamides, thiurams, dithiocarbamates, guanidines and thioureas.

Sensitizers are contemplated to include trialkyl cyanurate, trialkyl isocyanurate, trimethylolpropane trimethacrylate, ethylene glycol dimethacrylate.

The concentration of the covalent crosslinking agent in the organic solution or carrier is about 0.1 to about 20 weight percent, more preferably about 0.15 to about 15 weight percent and most preferably about 0.17 to about 10 weight percent. The curing of the coating of the carboxylated polymer with the covalent crosslinking agent occurs during the afore-mentioned drying step of the process at temperatures above 40° C.

In the process of curing the carboxylated polymeric coating with an electron beam, the coating is first dried in the aforementioned drying step of the process. The dried carboxylated polymeric coating is cured by exposure to an electron beam radiation at ambient temperature for a sufficient period of time (10 to 60 minutes) to cause covalent crosslinking, wherein the electron beam is 1 to 50 MRad, preferably 2. to 25, and most preferably 5 to 20.

Where sulfur monochloride is employed as the crosslinking agent, there are several approaches which may be sued to crosslink the coating. In a first embodiment, the substrate particles coated with the dried carboxylated polymeric coating is covalently crosslinked by exposing the coated particles to a saturated vapor of sulfur monochloride at ambient temperature for a sufficient period of time, 1 hour to 48 hours, more preferably 2 to 36 hours, and most preferably 10 to 30 hours, to cause covalent crosslinking. The coated polymer particles may be exposed to vapor by placing them on a screen in a desiccator or in a packed column and exposing the particles to the vapor for a period of time sufficient to cause covalent crosslinking of the sulfonated polymer.

In another variation of this process, the coated particles may be covalently crosslinked by contact with a solution of sulfur monochloride in an organic solvent selected from the group consisting of aliphatic, aromatic and halogenated hydrocarbons. The concentration of sulfur monochloride in the solution should be about 1 to about 50 weight percent, more preferably 2 to 40 weight percent, and most preferably 3 to 30 weight percent. The amount of sulfur monochloride solution used to cross-link the polymer contains enough sulfur monochloride to equal about 1.0 to about 20 weight percent of the weight of polymer in the coating, more preferably about 2.0 to about 15 weight percent and most preferably about 3.0 to about 12 weight percent of the polymer. The solution can be sprayed onto the coated particles by any means which ensures uniform distribution and then the solution is permitted to evaporate.

In yet another embodiment, crosslinking with sulfur monochloride may be carried out by direct addition of sulfur monochloride to the sulfonated polymer solution immediately prior to spray coating. The amount of sulfur monochloride added may range from the weight of about 1.0 to about 20 weight percent based on the weight of the sulfonated polymer to which it is added, more preferably about 2.0 to about 15 weight percent and most preferably about 3.0 to about 12 weight percent of the polymer. The spray coating and drying process is then carried out as described above:

The ionically and covalently crosslinked carboxylated polymer coating can be used as a barrier to create desired slow release for many types of fertilizers, micronutrients or other solid materials either individually and/or in mixtures, suitable for purposes of the present invention including by way of example:

MACRONUTRIENTS

Nitrogen, for example provided by:
Ammonium sulphate
Ammonium chloride
Ammonium nitrate
Diammonium phosphate
Ammonium phosphate nitrate
Monoammonium phosphate
Ammonium phosphate sulphate
Sodium nitrate
Potassium nitrate
Calcium nitrate
Urea
Ammonium nitrate-calcium carbonate mixture
    Potassium, for example provided by:
Potassium nitrate
Sulphate of potash
Muriate of potash
Potassium metaphosphate
    Phosphorous, for example provided by:

Ammonium phosphate nitrate
Ammonium phosphate sulphate
Monoammonium phosphate
Diammonium phosphate
Single superphosphate
Triple superphosphate
Potassium metaphosphate
  Sulfur, for example provided by:
Ammonium sulphate
Ammonium phosphate sulphate
Sulphate potash
Calcium sulfate
Ammonium bisulphite
Ammonium phosphate
Ammonium polysulphide
Ferrous sulphate
Gypsum
Kalinite
Leonite
Magnesium sulphate
Polyhalite
Pyrite
Schoenite
Sodium sulphate
Sulphur
Sulphur dioxide
Single superphosphate
Urea sulphur
Zinc sulphate
  Calcium, for example provided by:
Calcium nitrate
Calcium sulfate
Calcium chloride

MICRONUTRIENTS

Boron as:
Borax (sodium tetraborate decahydrate)
Sodium tetraborate pentahydrate
Sodium tetraborate-pentaborate
Colemanite
  Copper as:
Cupric oxide
Curous oxide
Cupric sulphate nonahydrate
Ferrous sulphate heptahydrate
  Manganese as:
Manganous carbonate
Manganous oxide
Manganous-manganic oxide
Manganous sulphate monohydrate
  Molybdenum as:
Ammonium molybdate
Sodium molybdate (anhydrous)
Molybic oxide
  Zinc as:
Calcinated zinc concentrate
Zinc carbonate
Zinc oxide
Zinc sulphate monohydrate
Conventional slow release fertilizers may also be coated with the ionically and covalently crosslinked carboxylated polymers in accordance with the present invention, such as:

| Sulphur coated urea | Glycouril |
| Isobutylidene diurea | Magnesium ammonium |
| Crotonylidene diurea | phosphate (Mag Amp) |
| Urea formaldehyde | Guanyl urea sulphate |
| Trimethylene tetraurea | (GUS) |
| Oxamide | Guanyl urea phosphate |
| Cyanuric acid | (GUP) |
| Ammeline | Thiourea |
| Ammedlide | Phenylurea |

Urease or nitrification inhibitors can be included with the fertilizers. Examples of such inhibitors include urease inhibitors such as phenyl phosphoro-diamidate (PPD) and N-(n-butyl) thiophosphoric triamide (NBPT) and nitrification inhibitors such as N-serve (s-chloro-6-trichloromethyl pyridine) and decyandiamide (DCD).

The present invention is particularly suitable for combinations of the aforementioned fertilizers with any pesticide although the present invention can be practiced with fertilizers and/or pesticides alone. Examples of suitable pesticides include herbicides such as triallate and trifluralin, insecticides such as carbofuran and aldicarb, fungicides such as captan and benomyl, rodenticides such as warfavin and chlorophacinone, o-ethyl s,s-dipropyl phosphoradithioate, nematicides such as o,o-dethyl o-(p-methylsulfinyl) phenyl phosphorate, ascaricides such as kelthane and plictran, and bacteriocides such as stryptomycin and terromycin.

The plant growth media to which the fertilizers and fertilizer-pesticide composites coated in accordance with the present invention may be applied include liquid cultures i.e., hydroponics, soil-less cultures and any mixture of sand, vermiculite, peat, perlite, or any other inert or relatively inert support, and soils which can be either irrigated or rainfed soils.

The seeds or plants envisioned to be fertilized by the instant invention include any species falling in the Plant Kingdom. Examples, of such include the following: cereals, such as wheat, maize (corn), rice, barley, oats; grasses such as bluegrass, fescues, bromegrass (for forage, seed and/or turf production); legumes such as alfalfa, soybean, bean, peas, lentils; oilseeds such as canola, palm, cotton, olive, flax; vegetables such as potatoes, lettuce, celery, carrot, onion, tomatoes, peppers; other broadleaf plants such as mint; coniferous and deciduous trees and shrubs and flowers such as chrysanthemum, roses and tulips.

It should be understood; however, that the inclusion of herbicides with fertilizers coated with ionically and covalently crosslinked carboxylated polymers are not inconsistent with the term vegetation enhancement agent which is intended to be applied to the desired or target plant. The fact that herbicide may kill undesired vegetation does not diminish its role as a vegetation enhancement agent for others, particularly the vegetation for which the fertilizer is intended.

The previously listed fertilizers, pesticides, either individually and/or in mixtures, may be coated with ionically and covalently crosslinked carboxylated polymers in accordance with the present invention. In this regard, the substrate of the vegetation enhancement agent for purposes of the present invention may be a member selected from the group consisting of macronutrients, micronutrients, nitrogen fertilizers including inhibitors of urease, nitrogen fertilizers including inhibitors of nitrification activity, slow release fertilizers, and pesticides, in addition to mixtures of a plurality of each of the macronutrients, micronutrients, nitrogen fertilizers including inhibitors of urease, nitrogen fertilizers including inhibitors of nitrification activity, slow release fertilizers and pesticides, as well as mixtures of members from each group of macronutrients, micronutrients, nitrogen fertilizers including inhibitors of urease, nitrogen fertilizers including inhibitors of nitrification activity, slow release fertilizers and pesticides. In addition, the fertilizers and fertilizer/pesticide combinations coated with ionically and covalently crosslinked carboxylated polymer in accordance with the present invention may be mixed with non-coated fertilizers and/or pesticides of the same or different composition. In this regard, the non-coated member may be selected from the group consisting of macronutrients, micronutrients, nitrogen fertilizers including inhibitors of urease, nitrogen fertilizers including inhibitors of nitrification activity, slow release fertilizers and pesticides in addition to mixtures of a plurality of each of the groups of vegetable enhancement agents as well as mixtures of one or more members of each of the previously mentioned groups. When this is the case, the fertilizer or fertilizer/pesticide combination coated with the ionically and covalently crosslinked carboxylated polymer in accordance with the present invention may comprise 5 to 95% by total weight of the mixture or the non-coated vegetation enhancement agent may comprise 5 to 95% by total weight of the mixture.

The plant growth media to which the fertilizers and fertilizer-pesticide composites coated in accordance with the present invention may be applied include liquid cultures, i.e., hydroponics, soil-less cultures and any mixture of sand, vermiculite, peat, perlite, or any other inert or relatively inert support, and soils which can be either irrigated or rainfed solids.

A variety of substrates which are discrete particulate solids may be encapsulated to form advantageous products. In some applications substrates are required to be released in a slow or controlled manner in given environments. Examples include: fertilizers, micronutrients, coated seeds, synthetic reagents or catalysts, pharmaceuticals and drugs. Substrates can also be modified by encapsulation in cases where their solid surfaces need to be more compatible when they are added to other materials. Examples are engineering plastics, adhesives or rubbers with incorporated filler particles, such as ground lime, carbon black, titanium dioxide, or zinc oxide.

The vegetation enhancement agent, i.e., fertilizer or fertilizer/pesticide combination, to which the present invention is applicable is preferably in a substantially solid form, i.e., particles, having a dimension, and preferably a major dimension, within the range of about 1.0 to 10.0 mm. Preferably, the fertilizer particles are granules having a diameter within the range of about 1.0 to 6.0 mm and most preferably about 1.0 to about 3.5 mm. Commercial fertilizer granules typically have a diameter of about 2.3 mm, although particles, such as granules having a diameter as large as about 6 mm, have been found to be useful, particularly for purposes of aerial application, for example used in the forestry industry.

Although the present invention has been described in connection with coating a vegetation enhancement agent, such as fertilizers/pesticide combinations, with a layer or film of ionically and covalently crosslinked carboxylated polymer, it should be understood that the present invention may also be used to coat a previously coated fertilizer or fertilizer/pesticide combination, such as conventional slow release fertilizers. Alternatively, fertilizers coated with ionically and covalently crosslinked carboxylated polymers in accordance with the present invention may also be coated with a conventional slow release coating, to which additional applications of the ionically and covalently crosslinked carboxylated polymer films or coatings in accordance with the present invention may be applied. Thus, a multiple-coated fertilizer or fertilizer/pesticide combination may be produced in accordance with the present invention. In this regard, however, it is preferred that the film or coating of the ionically and covalently crosslinked carboxylated polymer or interpolymer complex be either in direct contact with the vegetation enhancement agent, or form the exterior surface of the coated composite.

The present invention is also directed to agricultural processes, such as those for the enhancement of vegetation or vegetable matter. As used herein, vegetable matter is meant to be a division of nature comprising the plant kingdom as distinguished from matter of animal and mineral origin. Thus, vegetable matter includes seeds and plants, including seedlings, young plants, or any organ from which a plant can be generated, including naturally promulgated vegetable matter in addition to genetically engineered vegetable matter.

More specifically, the process of the present invention is directed to the stimulation of the germination and growth of a seed or a plant, including seedlings, young plants or any organ from which a plant can be generated, which involves the step of exposing the vegetable matter, e.g., the seed or plant, and/or the plant growth medium, i.e., soil, water and the like, either before, simultaneously with, or after the addition of the seed or plant to the plant growth medium to a fertilizer and/or fertilizer-pesticide combinations having a thin layer of a carboxylated polymer coated thereon.

In addition, the process also relates to the intimate admixing of fertilize, such as urea, ammonical, phosphorus and/or sulphur fertilizers, alone or combined with pesticides, with a seed or plant, or other vegetable matter, as defined herein, without damage to the same in a plant growth medium which involves the steps of:

1) admixing or otherwise contacting a fertilizer, preferably in solid granular form, having a thin ionically and covalently crosslinked carboxylated polymer or interpolymer complex film or coating thereon with a seed or plant;

2) placing such a fertilizer in close proximity to the seed or plant with or without a separation of time between the fertilizer and seedling steps.

In this regard, it has been discovered that fertilizers with thin films or coatings of ionically and covalently crosslinked carboxylated polymers, for example urea and ammonium sulfate, can be placed with the seed at the rate exceeding 25 kgN/ha without damage to the seed, seedlings, or young plants. Thus, the fertilizer and fertilizer/pesticide combinations having thin films or coatings of ionically and covalently crosslinked carboxylated polymers have been found to be extremely effective in stimulating seedling emergence and early plant growth by permitting the placement of urea fertilizers with the seed at the time of planting. It has been discovered that the thin ionically and covalently crosslinked carboxylated polymer film or coating slows the release of urea and ammonium to a sufficient extent to prevent burning of the seed or young seedling to which such a fertilizer is applied. In contrast to conventional slow release fertilizers, for example, urea coated with a thin film of ionically and covalently crosslinked carboxylated polymer in accordance with the present invention can be applied to the plant growth media at a rate in excess of 25 kgN/ha without raising the pH of the seed in the plant media a sufficient extent to burn the seed and prevent emergence.

Although phosphorous fertilizers are routinely seed-placed and have been found to be effective in stimulation of emergence and yield, known as the "pop-up" effect, seed-placing has not believed to have been possible with conventional ammonical nitrogen fertilizers prior to the development of the ionically and covalently crosslinked carboxylated polymer coated fertilizers and fertilizer/pesticide combination in accordance with the present invention. Thus, the carboxylated polymer coated fertilizers and fertilizer/pesticide combinations in accordance with the present invention have been found to be particularly advantageous in promotion of emergence, and early growth stimulation of seedlings, while permitting placement of the fertilizer with the seed.

Although the coated fertilizer of the present invention has been found to be particularly advantageous in permitting the introduction of nitrogen fertilizers and fertilizer/pesticide combinations simultaneously into the soil with the seed so as to stimulate emergence of seedlings and the growth of plants, fertilizers coated in accordance with the present invention may also preferably contain a source of sulfur and phosphorous, in which case, the fertilizer may be applied so as to supply nitrogen at a rate in excess of 25 kg/ha, sulfur in excess of 15 kg/ha, and phosphorous at a rate in excess of 30 kg/ha without burning the seeds or preventing subsequent emergence of the seedlings.

The present invention, therefore, is particularly suitable for replacing split or multiple applications of uncoated fertilizers to ensure that the available plant nutrient matches the physiological need of the crop for the same. In this regard, plants do not require all of their nitrogen at one time; for example, wheat requires over 35% of its nitrogen between booting and the soft touch stage. Typically uncoated fertilizers are applied in split applications at key physiological plant growth stages such as tillering, stem elongation, booting and seed filling to ensure that the nitrogen is available to the plant as required. Controlled release nitrogen, therefore, is effective in replacing split fertilizer applications. Controlled release nitrogen holds the nitrogen in a form until the nitrogen is needed by the plant. It has been discovered that the sulfonated polymer coated fertilizer and fertilizer/pesticide combinations in accordance with the present invention are particularly suitable for introduction with the seed and/or into the plant growth median during a single agricultural step so as to eliminate the need for post emergence application of the fertilizer.

The fertilizer and fertilizer/pesticide combination coated with thin films of ionically and covalently crosslinked carboxylated polymers in accordance with the present invention, however, may also be introduced into the soil prior to a subsequent planting of the seeds. For example, the coated fertilizer of the present invention may be introduced into the soil in the Fall of a year prior to planting wheat in the Spring of the following year, without appreciable loss of nutrients. Thus the coated fertilize of the present invention may be formulated so as to supply nitrogen at a sufficient rate and timing of release to satisfy the physiological need for nitrogen of the wheat beginning in the Spring of the year when the wheat is sown through the growing season. The coated fertilizer of the present invention may also be applied in a single application to supply nitrogen at a rate and timing of release essentially the same as provided by separate applications of fertilizer prescribed under a standard intensive cereal management program (ICM) thereby eliminating the need for multiple fertilizer applications which would otherwise be required by such an ICM program.

In view of the foregoing, it is believed that the ionically and covalently crosslinked carboxylated polymer coating of fertilizers in accordance with the present invention, and particularly phosphate fertilizers, would effectively reduce the chemical immobilization of phosphorous as calcium or aluminum/ironphosphate, thereby making fertilizer phosphorous more plant available.

In accordance with the present invention, fertilizers and fertilizer/pesticide combinations with thin films or coatings of ionically and covalently crosslinked carboxylated polymers permits the fertilizer to be applied to the soil at a rate which is at least 10% less than a fertilization rate for a fertilizer not coated in accordance with the present invention determined by a standard soil testing method as being required for the particular crop in the soil of the particular region. Although the rate of fertilizer reduction may be as much as about 50% less than the fertilization rate otherwise required, typically the rate is reduced within the range of about 10-20% less than a conventional fertilization rate.

It has been discovered that fertilizers and fertilizer/pesticide combinations coated with thin films of ionically and covalently crosslinked carboxylated polymer experience reduced nitrogen losses. This is particularly true for urea and ammonium sulfate. Conventionally, nitrogenous fertilizers added to moist soils, i.e., soils where the moisture levels exceed ⅔ of field capacity, i.e., 22 kPa, are subject to a loss of nitrogen due to a variety of factors including: leaching into ground waters, the denitrification to $N_2O$ and/or $N_2$ gas, volatilization of ammonia gas, and immobilization into the active microbial biomass. It has been discovered that fertilizers coated with thin films of ionically and covalently crosslinked carboxylated polymers in accordance with the present invention experience substantially reduced losses of nitrogen by controlling the release of nitrogen by the coated fertilizer; thus, the amount of fertilizer nitrogen available at any particular time which would be subjected to the previously mentioned deleterious effects is minimized. An advantage of the present invention, therefore, is a reduction in the losses of, for example, ammonical nitrogen by chemical, physical and biological occurrences. Thus, the present invention has been found effective in increasing plant yields because more nitrogen is available for the needs of the plant, while decreasing pollution of ground water with fertilizer-derived nitrates, decreasing destruction of the ozone layer of the atmosphere due to fertilizer-derived $N_2O$, and increasing residual nitrogen to benefit subsequent crops planted during the normal course of agricultural rotation.

PREFERRED EMBODIMENT

The following Examples demonstrate the performance of a neutralized carboxylated polymer as a barrier coating.

EXAMPLE 1

Improved Barrier Properties Of Carboxylated Polymer Coatings

Two different grades of zinc-ethylene/methaacrylic acid carboxylated polymers (Surlyn 9910 and Surlyn 9970 made by DuPont Co.) were dissolved in boiling tetrahydrofuran (THF). The polymer concentration of each solution was 2 weight percent. These solutions were used for dip coating of the polymer over solid, dry urea samples in order to determine the barrier properties of the encapsulated urea to water extraction.

To determine barrier properties of films formed from solution, urea slides were coated for immersion tests. The procedures for preparing coated samples of urea slides and conducting immersion tests are described as follows:

Urea samples were prepared by depositing reagent grade urea (Fisher Scientific) over microscope glass slides. This was done by dipping glass slides into molten urea at a temperature of about 135°–145° C., followed by cooling and solidification of the urea layer. The urea layer was built up to about 7 mm by four to five successive dipping and cooling cycles. These urea samples were then coated by a polymeric film using a second dipping procedure. Urea slides were repeatedly dipped into polymer solutions, such as those described above, followed by drying in a vacuum oven at 70° C. for about 3 hours. The dipping and drying cycles were repeated until the film thicknesses shown in Table I were obtained. The carboxylated polymer solutions in THF were kept at an elevated temperature of 40°–60° C. during the dipping process to avoid polymer precipitation.

The barrier properties of the various polymeric films were determined by immersion of each coated urea slide in about 100 g of deionized water at room temperature. The amount of urea released into the water was determined by recovering the urea after evaporating the water. Each sample was initially immersed for 1 day, followed by immersion in fresh water for 3 days and for weekly intervals thereafter.

Table I shows the permeabilities of urea solution extracted from the coated slides which were immersed in water at room temperature. The permeabilities of the coating materials were determined by applying Fick's law of diffusion at steady state. Fick's law states that:

$$J_m = DA \frac{\Delta C}{\delta}$$

where $J_m$=mass flux (loss) through the film or membrane, A=transport area, $\Delta C$=concentration gradient, $\delta$=film or membrane thickness and D=membrane diffusivity constant which is equal to the ratio of permeability (P) over the solubility ratio (K) of urea in the membrane and in water.

The performance of the carboxylated polymer coatings was compared with that of two commercially used coating materials. The first commercial coating solution was a tung oil solution made by Formby of Mississippi at 30 weight percent solids in petroleum distillate. The second commercial coating solution was linseed oil modified polyurethane Type I made by Minwax Paint Co. of New Jersey at 45% solids in petroleum distillate. The two commercial coatings were cured at 70° C. for 48 hours after coating.

The permeability of urea solution through the carboxylated polymer films was found to be about 2 orders of magnitude lower than either that of tung oil or that of polyurethane. Tung oil and polyurethane were disclosed as release control coatings for water soluble fertilizers in U.S. Pat. Nos. 3,321,298 and 3,233,518.

The reason for scatter in the permeability data for the carboxylated polymer coatings shown in Table I is believed to be a result of the coating quality. Existence of pin holes will increase the apparent permeability as calculated above. One should, therefore, assume that the lowest number corresponds to a more perfect coating. Permeabilities for the other polymers in Table I do, on the other hand, agree with literature data for perfect coatings with these polymers.

This Example shows that encapsulated urea having a carboxylated polymer coating is much more resistant to extraction by water than is the urea encapsulated by commercially used coatings. One can, therefore, apply a thinner coating of the carboxylated polymer for equivalent results to obtain a cost advantage or the carboxylated polymer coatings can be useful for a slower release.

TABLE I

Permeability of Urea Solution from Coated Urea Slides in Water at Room Temperature

| | | | |
|---|---|---|---|
| 141-3 | Tung Oil | 75 | $4.3 \times 10^{-9}$ |
| 141-6 | Tung Oil | 125 | $7.6 \times 10^{-9}$ |
| 158-4 | Polyurethane | 100 | $1.3 \times 10^{-9}$ |
| 158-5 | Polyurethane | 40 | $2.1 \times 10^{-9}$ |
| S-9910 | Carboxylated Polymer | 70 | $4.2 \times 10^{-9}$ |
| S-9970-A | Carboxylated Polymer | 70 | $2.7 \times 10^{-11}$ |
| S-9970-B | Carboxylated Polymer | 70 | $2.8 \times 10^{-10}$ |

EXAMPLE 2

Fluidized Bed Process for Surlyn 9970 Coating

The Surlyn 9970 coated fertilizer granules are produced using the following contemplated procedure:

4 kg of 2 to 3 mm fertilizer granules are introduced into a fluid bed coating machine, including a Wurster insert, manufactured by Glatt Air Techniques Inc., model number GPCG-5. The fertilizer is fluidized by blowing 200 scfm of heated air (70° C.) through bed. After the bed reaches a temperature of 50° C., a 2.5 weight percent hot solution of the Surlyn 9490 polymer in toluene and methanol cosolvent and methyl isobutyl carbonal is sprayed onto the fertilizer granules at the Wurster insert entrance. The spray nozzle uses was a commercial two fluid nozzle using air at 2 bars pressure to form an atomized spray regime in the Wurster insert.

The spraying is continued at 300 gm/min (probably up to 500 gm/min) rate until the required thickness of polymeric coating is built up on the fertilizer, i.e. approximately 12 minutes per a coating level of 1 wt. % polymer on the fertilizer.

After the solution is sprayed onto the granules in the Wurster insert, the thus coated granules are blown by the heated air upwards into the drying section of the machine. Here, the solvents are evaporated by the hot air, leaving a thin coat of dried polymeric material on the granules. The dried granules fall back into the fluid bed and then re-enter the Wurster insert where the coating process is repeated. Thus, multiple films or layers of the Surlyn 9970 polymeric coating is built up until the spraying was stopped.

The spraying is continued until 5 wt. % Surlyn 9970 is added. The spraying is stopped and the coated granules are dried with the hot air for 5 minutes. The product is logged and is marked 5 wt. % of Surlyn 9970 on fertilizer.

EXAMPLE 3

The contemplated method for crosslinking the polymer using electron beams is as follows:

Granular fertilizer pellets in the size range of 2 to 3 mm coated with 5 wt. % per Surlyn 9970 are placed in a monolayer on a flat bed cart. The cart is placed in an electron beam generator until a dose of 10 Megarads is obtained.

EXAMPLE 4

The contemplated method for crosslinking Surlyn 9970 with sulfurmonochloride is as follows:

Approximately 100 g of coated pellets consisting of 5 wt. % Surlyn 9970 on 2–3 mm granular fertilizer are placed in a monolayer in a flat dish. The dish was then put into a desiccator which contains a separate dish with 0.5 grams of liquid sulfur monochloride. The desiccator is closed and evacuated so that only sulfur monochloride vapor remains. The pellets are left in the desiccator for 24 hours. After that they are removed and placed in a vacuum oven at 40° C. for 10 to 12 hours in order to remove residual sulfur monochloride.

What is claimed is:

1. A composite comprising:
   (a) a urea substrate; and
   (b) a polymeric coating adhered to at least one surface of said substrate, said polymer coating having a thickness of about 1 to about 100 micrometers, wherein said polymer coating comprises an ionically and covalently crosslinked, neutralized carboxylated polymer having a carboxylate content of about 5 to about 300 meq. per 100 grams of said covalently crosslinked, neutralized carboxylated polymer, wherein the carboxylated polymer is characterized by the structure:

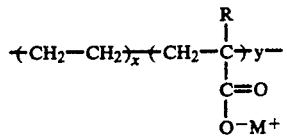

wherein y is about 0.1 to about 30 mole percent, and x+y equals 100 mole percent; R is methyl; $M^+$ is a Group IA metal.

2. The composite according to claim 1 wherein said carboxylate groups are neutralized with an ammonium or metal counterion.

3. The composite according to claim 2 wherein said metal counterion is selected from the group of transition elements and Groups IA, IIA, IB and IIB of the Periodic Table of Elements.

4. The composite according to claim 3 wherein the carboxylate groups are at least 20 mole percent neutralized.

5. The composite according to claim 1 wherein the substrate is a fertilizer.

6. A method for treating seeds or plants which comprises placing in close proximity thereto a composite comprising (i) a substrate selected from the group consisting of fertilizers, pesticides, herbicides, nutrients and mixtures thereof, and (ii) a polymeric coating adhered to at least a portion of the surface of the substrate, said coating having a thickness of about 1 to 100 micrometers and comprising an ionically and covalently crosslinked, neutralized carboxylated polymer having a carboxylate content of about 5 to about 300 meq./100 grams of said carboxylated polymer, wherein the carboxylated polymer is characterized by the structure:

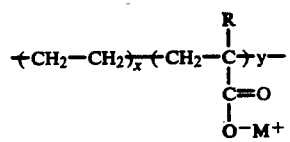

wherein y is about 0.1 to about 30 mole percent, and x+y equals 100 mole percent; R is methyl; and $M^+$ is a Group IA metal.

7. The method of claim 6 wherein the substrate comprises a fertilizer.

8. The method of claim 7 wherein the treat rate exceeds 25 kg/ha.

* * * * *